US00RE35648E

United States Patent [19]

Tenerz et al.

[11] E Patent Number: Re. 35,648

[45] Reissued Date of Patent: Nov. 4, 1997

[54] SENSOR GUIDE CONSTRUCTION AND USE THEREOF

[75] Inventors: Lars Tenerz; Dan Akerfeldt, both of Upsala, Sweden

[73] Assignee: Radi Medical Systems AB, Upsala, Sweden

[21] Appl. No.: 501,810

[22] Filed: Jul. 13, 1995

Related U.S. Patent Documents

Reissue of:

[64] Patent No.: 5,226,423
Issued: Jul. 13, 1993
Appl. No.: 728,142
Filed: Jul. 10, 1991

[30] Foreign Application Priority Data

Jul. 11, 1990 [SE] Sweden ..... 90 02416

[51] Int. Cl.[6] ..... A61M 25/00

[52] U.S. Cl. ..... 128/673; 128/772; 128/748; 604/280

[58] Field of Search ..... 128/637, 673, 128/675, 657, 772, 692, 748; 604/280–282, 164, 170

[56] References Cited

U.S. PATENT DOCUMENTS

| | | | |
|---|---|---|---|
| 3,710,781 | 1/1973 | Hutchins, IV et al. | 128/675 |
| 3,946,724 | 3/1976 | LaBalme | 128/675 X |
| 4,787,396 | 11/1988 | Pidorenko | 128/675 X |
| 4,873,986 | 10/1989 | Wallace | 128/675 X |
| 4,953,553 | 9/1990 | Tremulis | 128/637 |
| 5,069,226 | 12/1991 | Yamauchi et al. | 128/772 |

FOREIGN PATENT DOCUMENTS

| | | |
|---|---|---|
| 0313836 | 5/1989 | European Pat. Off. . |
| 48-93187 | 12/1973 | Japan . |
| 57-136434 | 8/1982 | Japan . |
| 59-80257 | 5/1984 | Japan . |
| 89/10088 | 11/1989 | WIPO . |
| 90/01294 | 2/1990 | WIPO . |

*Primary Examiner*—Brian L. Casler
*Attorney, Agent, or Firm*—Foley & Lardner

[57] ABSTRACT

A sensor guide has a sensor element, an electronic unit, a signal transmitting cable connecting the sensor element to the electronic unit, a flexible tube having the cable and the sensor element disposed therein, a solid metal wire having a plurality of sections with differing thicknesses such that each of the sections has a different flexibility, and a coil which is attached to a distal end of the wire. An inside portion of the flexible tube acts as an air channel to establish communication between the sensor element and atmospheric pressure. In addition, the wire is rigidly disposed in the sensor guide and extends along the entire sensor guide inside of the tube. Moreover, one of the plurality of sections is an enlarged portion having a slot therein and the sensor element is disclosed in the slot between the coil and the proximal end of the wire.

26 Claims, 3 Drawing Sheets

SENSOR GUIDE CONSTRUCTION AND USE THEREOF

Matter enclosed in heavy brackets [ ] appears in the original patent but forms no part of this reissue specification; matter printed in italics indicates the additions made by reissue.

BACKGROUND OF THE INVENTION

The present invention relates to guide construction and the use thereof.

A sensor mounted on a guide to be used for pressure measuring in stenotic vessels belonging to atherosclerotic patients is described in patent application WO 90/01294. Briefly, the known sensor guide construction comprises a cannula tube for establishing an air channel from the sensor to atmospheric pressure. The drawback of the cannula tube is that it easily takes form when it passes strong bends. Furthermore, the known sensor guide construction requires the mounting of several tubes, having different dimensions, over each other to obtain different flexibility and that security threads are attached in the ends of the tubes. This kind of tube assembly is also described in EP A2 313 836 and involves a complex production process.

In WO 89/10088 there is described a guide wire for catheters, but since this does not comprise a sensor it does not solve the problems with establishing an air channel as described above.

SUMMARY OF THE INVENTION

An object of the invention is to provide a sensor guide construction which is less sensitive to mechanical stress and which is easier to produce from a production technical point of view.

The above object is met by providing a sensor guide having a sensor element, an electronic unit, a signal transmitting cable connecting the sensor element to the electronic unit, a flexible tube having the cable and the sensor element disposed therein, a solid metal wire having a plurality of sections of differing thicknesses such that each of the sections has a different flexibility, and a coil which is attached to a distal end of the wire. An inside portion of the flexible tube acts as an air channel to establish communication between the sensor element and atmospheric pressure. In addition, the wire is rigidly disposed in the sensor guide and extends along the entire sensor guide inside of the tube. Moreover, one of the plurality of sections is an enlarged portion having a slot therein and the sensor element is disposed in the slot between the coil and the proximal end of the wire.

BRIEF DESCRIPTION OF THE INVENTION

The invention will now be described more closely below in connection to the accompanying drawings in which FIG. 1 is a longitudinal section view of a sensor guide construction according to the present invention;

DETAILED DESCRIPTION OF THE PREFERRED EMBODIMENT

Figure 1:
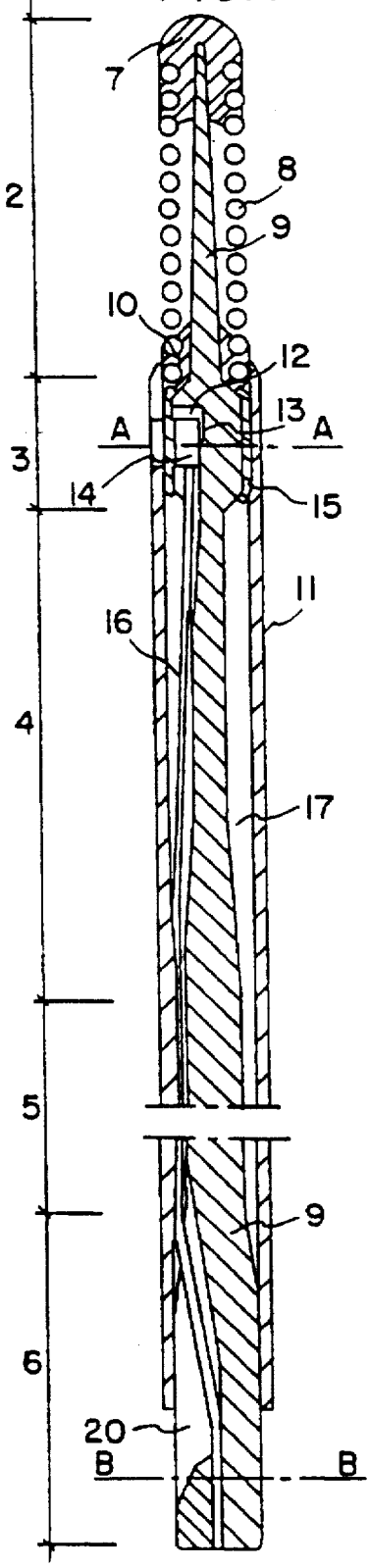

In FIG. 1 a sensor guide construction according to the present invention is shown. The sensor guide construction 1 has, in the drawing, been divided into five sections, 2–6, for illustrative purposes. The section 2 is the most distal portion, i.e. that portion which is going to be inserted fartherst into the vessel, and section 6 is the most proximal portion, i.e. that portion being situated closest to a not shown electronic unit. Section 2 is about 10–50 mm, section 3 about 1–5 mm, section 4 about 200–400 mm, section 5 about 1000–2000 mm and section 6 about 10–100 mm.

Section 2 comprises a radiopaque coil 8, being made of e.g. platinum, provided with an arced tip 7 being or alternatively welded thereon. In the platinum coil 8 and respectively in tip 7, there is also attached a stainless, solid metal wire 9 which in section 2 is formed like a thin conical tip and functions as a security thread for the platinum coil 8. The successive tapering of the metal wire 9 in section 2 towards the arced tip 7 results in that the front portion of the sensor guide construction becomes succesively softer. The tapering is obtained by cylindrical grinding of the metal wire 9.

At the transition between the sections 2 and 3 the lower end of the coil 8 is attached to the wire 9 with glue or alternatively, solder, thereby forming a joint 10. At the joint 10 a thin outer tube 11 commences which is made of a biocompatible material, e.g. polyimid, and extends downwards in the FIGURE all the way to section 6. The tube 11 has been treated to give the sensor guide construction a smooth outer surface with low friction. The metal wire 9 is heavily expanded in section 3 and is in this expansion provided with a slot 12 in which a sensor element 14 is arranged, e.g. a pressure gauge. The expansion of the metal wire 9 in which the sensor element 14 is attached decreases the stress, exerted on the sensor element 14 in sharp vessel bends. Preferably a recess 13 is arranged in the slot 12, providing an extra deep area under the site of the pressure sensitive part of the sensor element 14 so that the sensor element will not experience any mechanical stress if the wire 9 is bent, i.e. the recess forms a clearance for the sensor element 14.

The recess 13 and the slot 11 are made by spark machining in the metal wire 9. The slot 12 has the approximate dimensions 100 μm width×100 μm depth. The length of the slot can be varied as desired. The sensor element 14 is sealed against surrounding blood pressure with a hose 15 covering the expansion of the wire 9 The hose 15 functions as a soft membrane and is made of a flexible material. On the outside of the sensor element 14 and the hose 15, and lying thereover, is an opening arranged in the tube 11, so that the sensor element comes in contact with the environment in order to perform, for example, pressure measuring.

From the sensor element 14 there is arranged a signal transmitting cable 16 which can be an optic fiber or electric cables 16. The signal transmitting cable 16 extends from the sensor element 14 to a not shown electronic unit being situated below the section 6. The metal wire 9 is substantially thinner in the beginning of section 4 to obtain good flexibility of the front portion of the sensor guide construction. Between the tube 11 and the metal wire 9 there is also an air channel 17 giving the sensor guide construction an atmosheric pressure in the slot 12 in which the sensor 14 is arranged. The air channel 17 begins in section 6 at the proximal end of the tube 11 and extends thereafter inside of the tube 11 to the sensor element 14 in the slot 12. The function of the tube 11 is to create the air channel 17 and enclose the cable 16. Furthermore the same tube 11 protects the hose 15, which according to prior art has been protected by a separate short steel tube. In the end of section 4 and in the whole of section 5, the metal wire 9 is thicker in order to make it easier to push the sensor guide construction 1 forward in the vessel. In section 6 the metal wire 9 is as coarse as possible to be easy to handle and is here provided with a slot 20 in which the cable 16 is attached with e.g. glue. The signal transmitting cable 16 is centrated in this second slot 20 which is especially important if the cable 16 is an optic fiber intended to be connected to another optic fiber by a conncection, as is described in our pending patent application with the title "Fiber optic connection and use thereof" to which is referred. In section 6 the air channel 17 communicates with atmospheric pressure via the slot 20 arranged here since the tube 11 is not covering the whole of this section.

Figure 2:
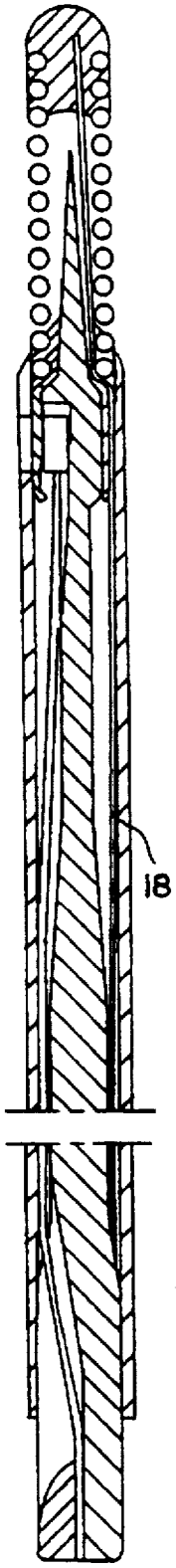
FIG. 2 is a section view similar to FIG. 1 of an alternative embodiment.

In the alternative embodiment shown in FIG. 2, the front portion of the metal wire 9 is not fastened in the tip 7 but in security thread 18 is arranged inside the tube 11 and at its distal end is attached in section 6 and at its prymid end is attached in the tip 7. Alternatively the front end of the metal wire can be attached in section 5.

Figure 3:
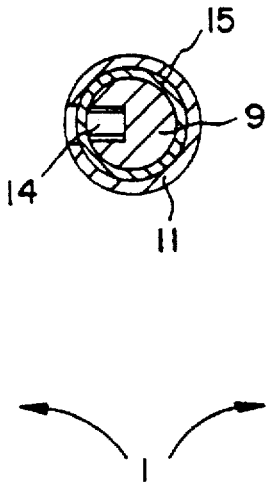
FIG. 3 is a section along line A—A in FIG. 1.

FIG. 3 is a cross section along line A—A in FIG. 1, showing the tube 11, the hose 15, the sensor element 14 in the slot 12 of the metal wire 9 and the opening in the tube 11 in front of the sensor element 14 to enable e.g. pressure measuring.

Figure 4:
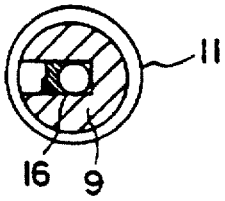
FIG. 4 is a section along line B—B in FIG. 1.

FIG. 4 shows the cross section along line B—B in FIG. 1 showing the fiber or cables 16 attached with an inner glueing in the front of the slot 20 of the metal wire 9. It is possible, as shown in FIG. 17, to have a single slot 21 which extends to entire length from the expansion in which the sensor element is attached down to the profined end of wire 9. The cable 16 and the air channel 17 are enclosed in this slot. Alternatively, the air channel can be arranged between the wire 9 and the tube 11 are included the two slots 12 and 20, situated in sections 3 and 6, respectively, as described above.

Figure 5:
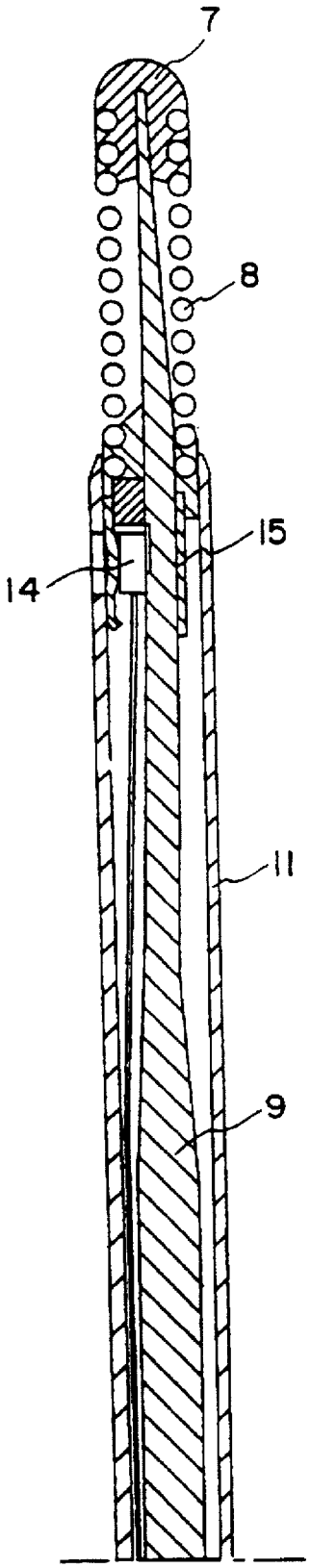
FIG. 5 is a section view of yet another alternative embodiment.

In FIG. 5, an alternative embodiment of the sensor guide construction according to the present invention is shown in mainly the same scale as the FIG. 1–4. The section 3 is substantially thinner in this embodiment than in the former. This means that section 3 of the sensor guide construction can be made smaller, which is advantageous with regard to production and use.

Figure 6:
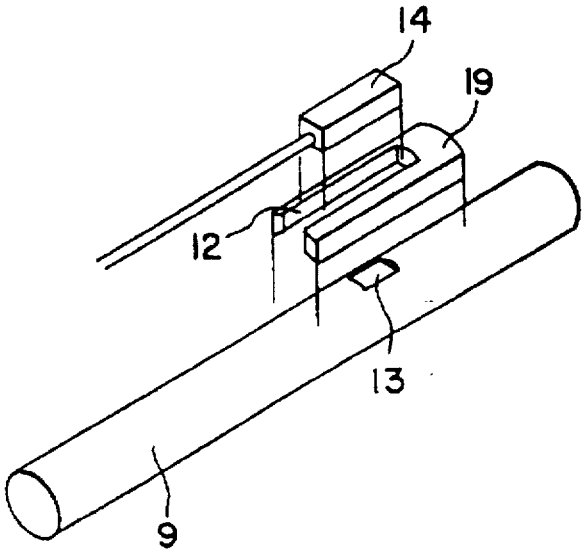
FIG. 6 is a schematic view showing the mounting of the embodiment shown in FIG. 5.
Figure 7:
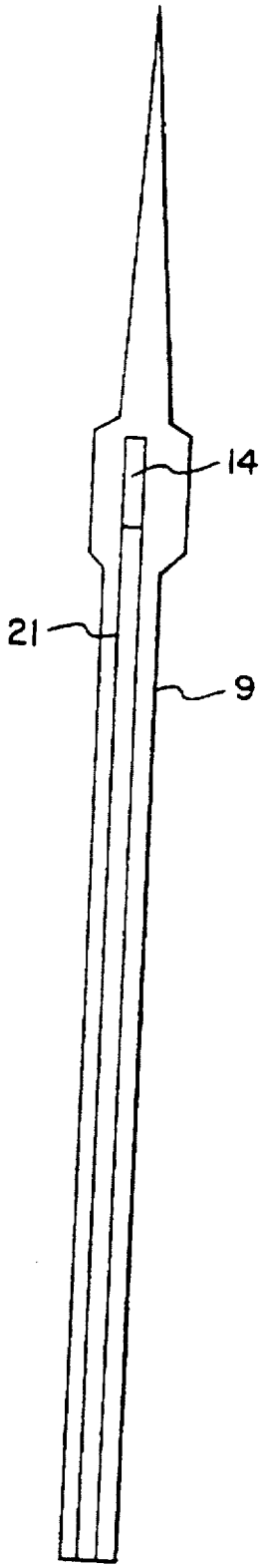
FIG. 7 is a schematic top plan view of a solid metal wire having a continuous slot from the position of the sensor element to the proximal end of the wire.

The production of section 3 of the sensor guide construction according to FIG. 5 is shown in FIG. 6. In a round solid wire 9 a recess 13 is spark machined. Over this, there is glued or soldered a previously obtained part 19 provided with the slot 12. The part 19 is obtained in that the slot having the same dimensions as the slot 12 is sparked out in a tube having the same inner diameter as the outer diameter of the metal wire 9. Thereafter the portion of the tube in which the slot is situated, is cut out, whereby the portion 19 according to FIG. 6 is obtained. It also appears where the sensor element 14, is going to be situated in the ready mounted construction according to FIG. 5.

The sensor guide construction according to the present invention does not take form after it has been bent. Different flexibility is obtained without complex production since only the coarseness of the metal wire 9 has to be varied. Furthermore the need of several security threads is avoided. The metal wire 9 consists preferably of memory metal or stainless steel.

The sensor element can be fiber optic or electric depending on whether the signal transmitting cable 16 is fiber optic fiber or electric cables.

Claims:

1. A sensor guide comprising:

a sensor element;

a signal transmitting cable adapted to connect said sensor element to an electronic unit;

a flexible tube having said cable and said sensor element disposed therein, an inside portion of said tube acting as an air channel to establish communication between said sensor element and atomspheric pressure;

a solid metal wire having a distal end, a proximal end, and a plurality of sections each having a different thickness such that each of said plurality of sections has a different flexibility; and a coil attached to said distal end of said wire wherein 1) said wire is rigidly disposed a said tube and extends along the entire sensor guide inside said tube, 2) one of said plurality of sections is an enlarged position having a slot therein, and 3) said sensor element is disposed in said slot between said coil and said proximal end.

2. A sensor guide as recited in claim 1, wherein said coil is a radiopague coil and is connected to said tube via a glue or welded joint.

3. A sensor guide as recited in claim 2 wherein said coil is made from platinum.

4. A sensor guide as recited in claim 1, wherein said cable is an optic fiber cable and said sensor element is an optic sensor.

5. A sensor guide as recited in claim 1, wherein said cable is an electric cable and said sensor element is an electric sensor.

6. A sensor guide as recited in claim 1, wherein said wire is made from a memory metal.

7. A sensor guide as recited in claim 1, wherein said sensor element further comprises means for measuring intravascular pressure.

8. A sensor guide as recited in claim 1, further comprising a hose made from a flexible polymer material which is disposed around said enlarged portion of said wire and within said tube, and wherein said tube has an opening therein which is aligned with said sensor element such that said hose is disposed between said tube and said sensor element.

9. A sensor guide comprising:

a sensor element;

a signal transmitting cable adapted to connect said sensor element to an electronic unit;

a flexible tube having said cable and said sensor element disposed therein, an inside portion of said tube acting as an air channel to establish communication between said sensor element and atmospheric pressure;

a solid metal wire having a distal end and a plurality of sections each having a different thickness such that each of said plurality of sections has a different flexibility, said wire being rigidly disposed in said tube and extending along the entire sensor guide inside said tube;

a coil attached to said distal end of said wire; and a security thread attached to said coil and to said wire, said security thread extending inside of said tube.

10. A sensor guide comprising:

a sensor element;

a signal transmitting cable adapted to connect said sensor element to an electronic unit;

a flexible tube having said cable and said sensor element disposed therein, an inside portion of said tube acting as an air channel to establish communication between said sensor element and atmospheric pressure;

a solid metal wire having a plurality of sections each having a different thickness such that each of said plurality of sections has a different flexibility, said wire being rigidly disposed in said tube and extending along the entire sensor guide inside said tube;

a piece having a slot therein and a bottom surface with the same radius of curvature as an outside radius of curvature of said wire, said piece being attached at said bottom surface to an outer circumference of said wire and said sensor element being disposed in said slot.

11. A sensor guide comprising:

a sensor element;

a signal transmitting cable adopted to connect said sensor element to an electronic unit;

a flexible tube having said cable and said sensor element disposed therein, an inside portion of said tube acting as an air channel to establish communication between said sensor element and atmospheric pressure; and a solid metal wire having a proximal end and a plurality of sections each having a different thickness such that each of said plurality of sections has a different flexiblity, said wire being rigidly disposed in said tube and extending along the entire sensor guide inside said tube;

wherein said wire has first and second slots therein, said wire is disposed in said tube, said air channel is a space existing between said tube and said wire, said air channel extends from said first slot to said second slot, said sensor element is disposed in said first slot, and said second slot is disposed in a proximal end of said wire and is in communication with atmospheric pressure.

12. A sensor guide comprising;

a sensor element;

a signal transmitting cable adopted to connect said sensor element to an electronic unit;

a flexible tube having said cable and said sensor element disposed therein, an inside portion of said tube acting as an air channel to establish communication between said sensor element and atmospheric pressure;

a solid metal wire having a proximal end and a plurality of sections each having a different thickness such that each of said plurality of sections has a different flexibility, said wire being rigidly disposed in said tube and extending along the entire sensor guide inside said tube;

wherein said wire has a slot therein having first and second ends, said sensor element is disposed in said slot at said first end, said second end is disposed at said proximal end of said wire, and said air channel is defined between an inner surface of said tube and said slot.

13. A sensor guide as recited in claim 10, wherein said slot includes a recessed portion located below said sensor element.

*14. A sensor guide comprising:*

*a sensor element;*

*a signal transmitting cable adapted to connect said sensor element to an electronic unit;*

*a flexible tube having said cable and said sensor element disposed therein;*

*a solid metal wire having a distal end, a proximal end, and a plurality of sections each having a different thickness such that each of said plurality of sections has a different flexibility; and*

*a coil attached to said distal end of said wire;*

*wherein 1) said wire is rigidly disposed in said sensor guide and extends along the entire sensor guide inside said tube, 2) one of said plurality of sections is an enlarged portion having a slot therein, and 3) said sensor element is disposed in said slot between said coil and said proximal end.*

*15. A sensor guide as recited in claim 14, wherein said coil is a radiopaque coil and is connected to said tube via a glue or welded joint.*

*16. A sensor guide as recited in claim 15, wherein said coil is made from platinum.*

*17. A sensor guide as recited in claim 14, wherein said cable is an optic fiber cable and said sensor element is an optic sensor.*

*18. A sensor guide as recited in claim 14, wherein said cable is an electric cable and said sensor element is an electric sensor.*

*19. A sensor guide as recited in claim 14, wherein said wire is made from a memory metal.*

*20. A sensor guide as recited in claim 14, wherein said sensor guide further comprises means for measuring intravascular pressure.*

*21. A sensor guide as recited in claim 14, further comprising a hose made from a flexible polymer material which is disposed around said enlarged portion of said wire and within said tube, and wherein said tube has an opening therein which is aligned with said sensor element such that said hose is disposed between said tube and said sensor element.*

*22. A sensor guide comprising:*

*a sensor element;*

*a signal transmitting cable adapted to connect said sensor element to an electronic unit;*

*a flexible tube having said cable and said sensor element disposed therein;*

*a solid metal wire having a distal end and a plurality of sections each having a different thickness such that each of said plurality of sections has a different flexibility, said wire being rigidly disposed in said sensor guide and extending along the entire sensor guide inside said tube;*

*a coil attached to said distal end of said wire; and*

*a security thread attached to said coil and to said wire, said security thread extending inside of said tube.*

*23. A sensor guide comprising:*

*a sensor element;*

*a signal transmitting cable adapted to connect said sensor element to an electronic unit;*

*a flexible tube having said cable and said sensor element disposed therein;*

*a solid metal wire having a plurality of sections each having a different thickness such that each of said plurality of sections has a different flexibility, said wire being rigidly disposed in said sensor guide and extending along the entire sensor guide inside said tube;*

*a piece having a slot therein and a bottom surface with the same radius of curvature as an outside radius of curvature of said wire, said piece being attached at said*

*bottom surface to an outer circumference of said wire and said sensor element being disposed in said slot.*

*24. A sensor guide as recited in claim 23, wherein said slot includes a recessed portion located below said sensor element.*

*25. A sensor guide comprising:*

*a sensor element;*

*a signal transmitting cable adapted to connect said sensor element to an electronic unit;*

*a flexible tube having said cable and said sensor element disposed therein; and*

*a solid metal wire having a proximal end and a plurality of sections each having a different thickness such that each of said plurality of sections has a different flexibility, said wire being rigidly disposed in said tube and extending along the entire sensor guide inside said tube;*

*wherein said wire has first and second slots therein, said wire is disposed in said tube, said sensor element is disposed in said first slot, and said second slot is disposed in a proximal end of said wire.*

*26. A sensor guide comprising:*

*a sensor element;*

*a signal transmitting cable adapted to connect said sensor element to an electronic unit;*

*a flexible tube having said cable and said sensor element disposed therein;*

*a solid metal wire having a proximal end and a plurality of sections each having a different thickness such that each of said plurality of sections has a different flexibility, said wire being rigidly disposed in said tube and extending along the entire sensor guide inside said tube;*

*wherein said wire has a slot therein having first and second ends, said sensor element is disposed in said slot at said first end, said second end is disposed at said proximal end of said wire.*

* * * * *